United States Patent
Gouge et al.

[11] Patent Number: 5,253,759
[45] Date of Patent: Oct. 19, 1993

[54] CONTAINERIZATION SYSTEM

[75] Inventors: Samuel T. Gouge; James E. Shue, both of Raleigh, N.C.

[73] Assignee: Rhone-Poulenc Inc., Research Triangle Park, N.C.

[21] Appl. No.: 859,112

[22] Filed: Mar. 27, 1992

Related U.S. Application Data

[63] Continuation-in-part of Ser. No. 680,301, Apr. 4, 1991, abandoned, and a continuation-in-part of Ser. No. 679,290, Apr. 2, 1991, abandoned, and a continuation-in-part of Ser. No. 713,684, Jun. 11, 1991, abandoned.

[51] Int. Cl.$^5$ ..................... B65D 81/32; B65D 85/82
[52] U.S. Cl. ..................... 206/524.7; 71/DIG. 1; 206/205; 206/568; 252/315.1; 424/409
[58] Field of Search ............... 71/DIG. 1; 206/0.5, 206/204, 205, 219, 524.1, 524.2, 524.6, 524.7, 525, 568; 252/315.1; 424/409, 412; 514/801, 812

[56] References Cited

FOREIGN PATENT DOCUMENTS

| | | | |
|---|---|---|---|
| 0132726 | 2/1985 | European Pat. Off. | 206/524.7 |
| 8912587 | 12/1989 | PCT Int'l Appl. | 206/524.7 |
| 0922317 | 3/1963 | United Kingdom | 206/524.7 |

*Primary Examiner*—Jimmy G. Foster
*Attorney, Agent, or Firm*—James G. Passé

[57] ABSTRACT

The present invention relates to a containerization system comprising at least one inner cold water soluble bag located within an outer cold water soluble bag. Each cold water soluble bag independently contains an agrochemical that does not substantially dissolve the bag, or bags, which it contacts. Typical agrochemicals are in solid, substantially non-aqueous liquid, or organic gel form. The inner bag contains an agrochemicals such as plant protection compounds, pesticides, fungicides, insecticides, acaricides, nematocides, herbicides, plant nutrients or plant growth regulators. The outer bag contains agrochemicals such as penetrating agents, synergists, antidotes, sticking agents, spreaders, plasticizers.

4 Claims, 1 Drawing Sheet

CONTAINERIZATION SYSTEM

This application is a continuation-in-part of U.S. Ser. No. 680,301, now abandoned, filed on Apr. 4, 1991, U.S. Ser. No. 679,290, now abandoned, filed on Apr. 2, 1991 and U.S. Ser. No. 713,684, now abandoned, filed on Jun. 11, 1991.

BACKGROUND OF THE INVENTION

I. Field of the Invention

The invention relates to a containerization system and to containers which are particularly suitable for storing, packaging and transporting toxic or hazardous products, e.g. agricultural chemical compounds, such as pesticides and concentrates thereof.

II. Discussion of the Prior Art

At present, most hazardous and toxic liquids are stored in metal drums or, where smaller quantities are involved, in plastic containers. Hazardous compounds, especially agrochemical compounds, are formulated in various compositions.

The expression toxic or hazardous compounds as used herein means an industrial chemical or agrochemical compound, which, if released in the quantity or concentration normally in storage and shipping containers, may cause damage to the environment or be injurious to a person contacted by it.

With respect to agricultural chemicals, liquid compositions, particularly in the form of concentrates, are most convenient for farmers because of the relative ease with which they can be handled. There are, nevertheless, difficulties in handling such liquid compositions. There is a danger of spillage or leakage if holes develop in containers that are accidentally dropped and thereby crack or fail. Containers have been developed which possess great resistance to impact and shock. While such containers are secure under normal storage and handling conditions, in the event of an accident, for example during transporting, there remains an appreciable risk of spillage or leakage with rapid loss of liquid. Leakage of toxic and hazardous chemicals can create damage to the environment.

The chemical and packaging industries have long sought a secure container which provides sufficient safeguard for those handling it, such as farmers and transporters, as well as adequate protection for the environment.

It is known, for example, to package agrochemicals in soluble bags or sachets made from water soluble films.

However there are some cases whereby the use of water soluble (or water dispersible, as always contemplated herein) bags is either impossible or of highly limited interest.

This is or can be the situation when two or more agrochemicals are used together to treat a crop or any kind of plant(s) and when only one of them is used in the form of a water soluble bag.

It is also or can be also the situation when two or more agrochemicals are used together to treat a crop or any kind of plant(s) and when the normal use of these agrochemicals is at a very different use rate. Indeed it is known that the use rate of some pesticides may vary in the order of 10 or even 100 times from one pesticide to another.

Another situation where the use of a water soluble bag for a pesticide has been considered up to now of no interest is the situation whereby incompatible agrochemicals are used. Incompatible agrochemicals are agrochemicals which, when added together in a concentrated form or in a tank for mixing, at least partially, agglomerate together and/or produce sediment at the bottom of the tank without being dispersed or emulsified in the tank when stirred.

In the art of detergency or laundry, it is known to use systems with one inner bag, or sachet, in an outer pouch (U.S. Pat. No. 4846992 or European patent application 132726), however these known systems comprise an outer water-permeable pouch or bag. Such water permeable pouches are in fact water-insoluble, and thus, they are not appropriate for uses wherein the whole containerization system has to disappear when put in water. This is especially the situation of farmers who disperse agrochemicals in water tank in order to obtain a spraying mixture.

Unfortunately the use of more than one agrochemical by farmers to treat their crop is more and more common, and the farmers like very much the so-called ready-mix which are mixtures that the farmers may use directly for dilution in their tank. Thus, the ready mix practice does not yet fit to the water soluble bag technology.

SUMMARY OF THE INVENTION

The present invention relates to a containerization system comprising at least one inner water soluble bag located within an outer water soluble bag. Each water soluble bag independently contains an agrochemical that does not dissolve the bag, or bags, which it contacts. Typical agrochemicals are in solid, liquid (preferred when substantially non-aqueous), or organic gel form. Typical agrochemicals include plant protection compounds such as pesticides (for example insecticides, fungicides, herbicides, acaricides, nematocides), plant nutrients or plant growth regulators; adjuvants for the activity for plants as activity promoters including penetrating agents, synergists, antidotes, sticking agents, spreaders, activators, compatibility agents; adjuvants for the water soluble bags as plasticizers.

An object of the instant invention is to provide a new containerization system to contain agrochemicals which is safe for everybody.

Another object of the instant invention is to provide a new containerization system to contain agrochemicals which is easy for the farmer to manipulate.

Another object of the instant invention is to provide a new containerization system to contain agrochemicals which is readily, rapidly and easily soluble and/or dispersible in water.

Another object of the instant invention is to provide a new containerization system to contain agrochemicals which is as much condensed as possible, using the least amount of space.

Another object of the instant invention is to provide a new containerization system and/or a new method to contain more than one hazardous compounds e.g. agrochemicals which diminishes the risks of pollution.

Another object of the instant invention is to provide a new containerization system to contain two or three hazardous compounds e.g. agrochemicals.

Another object of the instant invention is to provide a new containerization system to contain at least one agrochemical of the type plant protection agent on one side, and, separately from this first one, at least one agrochemical of the type adjuvant.

Another object of the instant invention is to provide a new containerization system to contain two or three hazardous compounds e.g. agrochemicals, which are normally used at different use rates.

Another object of the instant invention is to provide a new system to contain two or three hazardous compounds e.g. agrochemicals, which are normally incompatible.

Another object of the present invention is to provide a new system for containing chemicals such as agrochemicals which enables such chemicals to be easily and homogeneously dispersed in water even though they may be incompatible.

Another object of the present invention is to provide a new system for containing chemicals such as agrochemicals which enables such chemicals to be easily and homogeneously dispersed in water even though they may be present in a different or very different amount.

A further object of the present invention is to provide a containerization system wherein less solvent is needed in the formulation of an agrochemical, which is a cost saving both in shipping and manufacturing.

A further object of the present invention is to provide a new containerization system for agrochemicals which eliminates, or at least reduces the disagreeable odors or odor problems of odoriferous chemicals.

A further object of the present invention is to provide a new containerization system for agrochemicals which eliminates, or at least reduces, the waste disposal of contaminated containers and overpacks.

A further object of the present invention is to provide a new containerization system for agrochemicals which quickly dissolves when put into water.

The invention further seeks to provide a new containerization system for agrochemicals which reduces the risks of clogging the spray nozzles or the filters of spray tanks.

Other objects of the invention will better appear from the following description.

The objects of the invention can be achieved in full or in part by means of the invention.

BRIEF DESCRIPTION OF THE DRAWINGS

The containerization system of the present invention comprises at least one (preferably one or two) inner water soluble or water dispersible bags containing a hazardous compound or product, preferably an agrochemical, more preferably a non-aqueous agrochemical.

FIG. 1 and 2 illustrate, but are not intended to limit, the present invention.

Figure 1:
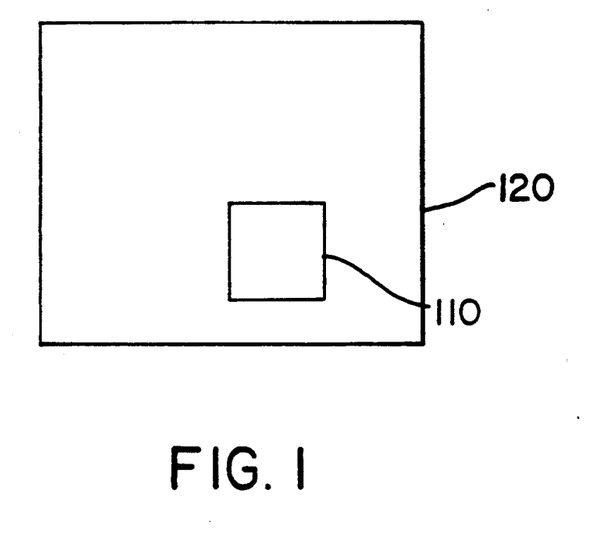
FIG. 1 is a front view which schematically shows an embodiment of the present invention having an inner bag 110 located within an outer bag 120.
Figure 2:
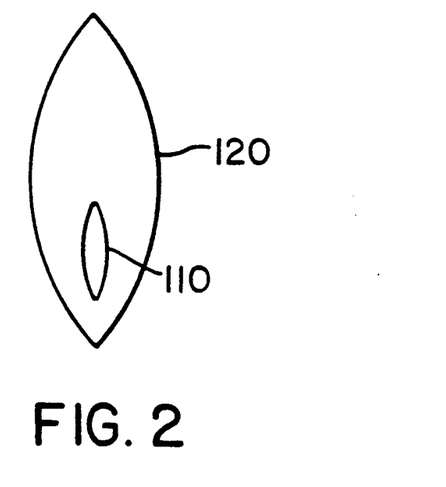
FIG. 2 is a side view of the embodiment of FIG. 1.

The containerization system further comprises an outer water soluble or water dispersible bag containing another hazardous compound or product (different from the first hazardous compound), preferably an agrochemical, more preferably a non-aqueous agrochemical. The outer bag also contains the inner bag with its content. Optionally, this so-called "poly-bag system" is itself contained in an external water insoluble container, such as a rigid or semi-rigid box.

A further speficity of the instant invention is that the containerization system comprises an outer water soluble bag and an inner water soluble bag containing two different kinds of agrochemical, one of the bags containing an agrochemical which is a plant protection agent (such as pesticides, e.g. insecticides, fungicides, herbicides, acaricides, nematocides), or plant nutrients or plant growth regulators, and the other bag containing an agrochemical of the adjuvant kind (such as activity promoters including penetrating agents, synergists, antidotes, sticking agents, spreaders, activators, compatibility agents; or adjuvants for the water soluble bags as plasticizers). The two kinds of agrochemicals used in the invention are in some way cooperating to improve the activity of the plant protection agent so as to increase this activity (synergists or plant penetrating agent), or to facilitate this activity (plant penetrating agent) or to improve this activity (sticking agents or spreaders) or to make this activity safer for the plant (antidotes) or for the bag (plasticizer of the polymeric material constituting the wall of the bag). The invention is thus particularly appropriate when the plant protection agent or plant nutrient or plant growth are incompatible. As already said, the adjuvant may be penetrating agent, synergist, antidote, sticking agent, spreader, activator, compatibility agent or plasticizer, but can also have more than one of these properties or effect.

The hazardous compounds or products of the invention and the wall of the bags they contact are chosen so that the hazardous compounds or products do not substantially dissolve the wall of the bag they contact and do not substantially permeate through it. By this it is meant that the dissolution and permeation are each independently less than 5%, more preferably less than 1% and most preferably less than 0.5% of the total weight of the bag.

The hazardous compounds of this invention, especially the agrochemical compositions, which are contained in the bags according to the invention are essentially materials containing 0.5 to 80% (w/w) of active ingredient and these agrochemical compositions are concentrated compositions which are supposed to be diluted in water before spraying.

The agrochemical compositions which may be used in the invention and which may be contained in the outer or the inner container may be in different physical forms. They may be in the form of a solid such as powders, preferably water wettable powders, or granules, preferably water dispersible granules; or they may be in the form of a nonaqueous liquid, such as a solution or a dispersion or an emulsion in an organic solvent; this liquid may be more or less viscous; it may be a very fluid liquid such as a liquid having a Brookfield viscosity between 100 and 1000 centipoise, or it may be a viscous liquid, such as a liquid having a Brookfield viscosity from 1000 up to 30000 centipoise (Measurements of viscosities in this specification are made with a Brookfield viscosimeter at 20° C. with a flat plate rotating at 20 revolutions per minute); a further advantageous physical form of the agrochemical composition is the form of an organic gel.

Gels which are of particular interest in the invention are organic gels which have viscosities of 600 to 30,000 centipoise, preferably 1,000 to 12,000 centipoise, and still more preferably 1,000 to 5,000 centipoise.

According to another aspect of the invention, the material or gel which is used in the invention is essentially a material which has a phase difference phi between the controlled shear stress and the resulting shear strain, such that tg(phi) is less than or equal to 1.5, preferably less or equal to 1.2. Tg(phi) is the tangent of the phi angle (or phase difference).

The measurement of phi is made by means of a dynamic rheometer. Dynamic rheometers which are appropriate to measure phi are known and available commercially. They usually have a flat fixed plate and a rotating cone or plate, or a so-called couette measuring system. Other mechanical systems are also available. Generally the choice of one system or another is made according to the recommandations of the seller of the rheometer, and is adapted to the kind of compound, gel or liquid, which is tested. The particular choice of a specific type of rheometer is something well known by the man skilled in the art of rheology. A rotating plate over another plate or a cone rotating over a plate are often more appropriate when a gel or a viscous liquid is tested. When two kinds of system for the rheometer are possible, similar values of phi are actually measured. The cone (or the plate or the couette) is caused to rotate by means of a controlled speed motor; the rotation is a sinusoidal one, i.e., the strain and the angular displacement change as a sine function with time. Tg(phi) is equal to the ratio $G''/G'$, wherein: $G'$ is the storage modulus (represents the behaviour of a perfect solid); $G''$ is the loss modulus (represents the behaviour of a perfect liquid). $G'$ and $G''$ are expressed in Pascal for a given rotational speed (radian per second).

$G'$ and $G''$, and thus tg(phi), may also depend on the amplitude of the oscillations (percentage of strain) of the rheometer; however, there is generally a so-called viscoelastic plateau whereby the values $G'$ and $G''$ of a gel do not depend substantially on the said amplitude; this means that in the conditions of the test under the viscoelastic plateau the structure of the gel is maintained and no destruction of the gel into a liquid happens. Of course, the measurement of $G'$ and $G''$ of a gel is made under the conditions of this viscoelastic plateau, just because it corresponds to the normal gel structure which is precisely what is tested.

$G'$ and $G''$, and thus tg(phi), may also depend on the speed of the oscillations (time to reach the chosen percentage of strain; expressed as radian per seconde) of the rheometer; however, when the gel is well structured, there is no so much variation from one speed to another. In order to have a reasonable measurement of the properties of a gel, it is generally preferred to operate in conditions whereby the gel is not too much stressed, that is to say at speed such as 1 radian per seconde. Of course, measurements at higher speed may also be made.

It is known that a gel is generally a colloid in which the dispersed phase has combined with the continuous phase to produce a viscous, jelly-like product; it is also a dispersed system consisting typically of a high molecular weight compound or aggregate of small particles in very close association with a liquid. The gels used in the invention have basically an organic continuous phase. In contrast, most of the existing materials/gels are water-based and have an aqueous continuous phase. Furthermore, the gels used in the invention have essentially one physical phase, at least as can be seen when visually observed. Preferred gels in the invention are also gels which can be divided by cutting and whose cut parts are able to merge together by simple juxtaposition.

The non aqueous agrochemical compositions which are used in the invention are essentially materials having a low water content, generally less than 5% (by weight), preferably less than 3%, more preferably less than 1%.

The choice of the particular physical form of the agrochemicals used in the invention depends on the particular agrochemicals which are involved.

The following features, alone or in combination, constitute preferred features of the invention:

According to one feature, the hazardous product is preferably an agrochemical, or more precisely a plant protection agent (including pesticides, such as insecticides, fungicides, herbicides, acaricides or nematocides; or plant growth regulators or plant nutrients).

The invention is not limited to some specific agrochemicals; a list of many agrochemicals which can be used in the poly-bag system of the invention includes:

fungicides such as triadimefon, tebuconazole, prochloraz, triforine, tridemorph, propiconazole, pirimicarb, iprodione, metalaxyl, bitertanol, iprobenfos, flusilazol, fosetyl, propyzamide, chlorothalonil, dichlone, mancozeb, anthraquinone, maneb, vinclozolin, fenarimol, bendiocarb, captafol, benalaxyl, thiram;

herbicides (or defoliants) such as quizalofop and its derivatives, acetochlor, metolachlor, imazapur and imazapyr, glyphosate and gluphosinate, butachlor, acifluorfen, oxyfluorfen, butralin, fluazifop-butyl, bifenox, bromoxynil, ioxynil, diflufenican, phenmedipham, desmedipham, oxadiazon, mecoprop, MCPA, MCPB, linuron, isoproturon, flamprop and its derivatives, ethofumesate, diallate, carbetamide, alachlor, metsulfuron, chlorsulfuron, chlorpyralid, 2,4-D, tribufos, triclopyr, diclofop-methyl, sethoxydim, pendimethalin, trifluralin, ametryn, chloramben, amitrole, asulam, dicamba, bentazone, atrazine, cyanazine, thiobencarb, prometryn, 2-(2-chlorobenzyl)-4,4-dimethyl-1,2-oxazolidin-3-one, fluometuron, napropamide, paraquat, bentazole, molinate, propachlor, imazaquin, metribuzin, tebuthiuron, oryzalin;

insecticides or nematicides such as ebufos, carbosulfan, amitraz, vamidothion, ethion, triazophos, propoxur, phosalone, permethrin, cypermethrin, parathion, methylparathion, diazinon, methomyl, malathion, lindane, fenvalerate, ethoprophos, endrin, endosulfan, dimethoate, dieldrin, dicrotophos, dichlorprop, dichlorvos, azinphos and its derivatives, aldrin, cyfluthrin, deltamethrin, disulfoton, chlordimeform, chlorpyrifos, carbaryl, dicofol, thiodicarb, propargite, demeton, phosalone; and plant growth regulators such as gibberellic acid, ethrel or ethephon, cycocel, chlomequat, ethephon, mepiquat; and penetrating agents such as high molecular weight hydrocarbon oil, for example limonene, paraffin based petroleum oil, polymerized pinene, oily paraffins, polyalkoxylated fatty alcohols, alkyl polyoxyethylene ether, free fatty acids, alkylaryl polyethoxylated ethanol, alkylaryl ethanol, polyol fatty acids esters, polyethoxylated polyol fatty acids esters, vegetable oil or gum, cottonseed oil, ethoxylated or polyethoxylated fatty amine, ethoxylated nonyl phenol, glycerol phtalate, alkyl polyoxyethylene glycols, alkylphenoxy polyoxyalkylene ether, poly-p-menthene, polymerized pyrophosphates, alkylaryl sulfonic acid salts or esters, alkylaryl polyoxyethylene glycol.

synergists are generally rather specific of a particular active ingredient, and thus, are known per se, antidotes or safeners are compounds as reducing the phytotxicity of agrochemicals or pesticides. They are generally specific of a particular pesticide, and thus, are known per se, stickers or spreaders such as phosphoric acid or its agronomically acceptable metallic salts, free fatty acids, alkylaryl alkoxylate, polyoxyethylene glycol phosphate esters, polyalkoxylated alcohol, alkyl polyethoxyethanol, alkylaryl polyethoxylated ethanol or propanol or isopropanol or butanol, dialkylarylpolyethoxy ethanol or glycerol, alkylaryl polyoxyethylene glycol, alkylaryl polyoxyethylene glycol ether, alkylaryl polyalkoxylated alcohols, bis(2-ethylhexyl)benzenedicarboxylate, methoxylated alkylcarboxylate, alkoxylated polyolester, alkylaryl sulfonate, polyoxyethylated nonyl or octyl phenol, nonylphenoxy polyethyleneoxy ethanol, 2-methoxy ethanol oleate, cotton seed oil, alkylphenoxy polyethoxy ethanol, ethoxylated alkyl aryl phosphate esters, alkylphenoxy polyethoxy ethanol phosphate, dialkylbenzene dicarboxylate, glycerol phtalate, polyethoxylated polyol fatty acid ester, polyol fatty acid ester, polyethoxylated fatty amine, dodecyl or dodecyloxy benzene or dibenzene sulfonate, di-menthene, polymenthene, limonene, alkylaryl propyl carbinols, polyoxyethylenepolyoxypropylene block copolymer, compatibility agents such as alkylaryl polyethoxyethyleneglycol phosphate ester, alkylaryl polyethoxyethylene ethanol phosphate ester, branched chain alcohol sulfate, sodium 2-ethylhexyl butanedioate, polyester of sodium thio butane dioate, isopropyl phosphate ester, ester of alkyl polyoxyethylene ethers, alkyl phenoxy polyethyleneoxy phenyl phosphate, plasticizers such as (this list is non limitative): alcohol compounds (linear or branched, saturated or unsaturated), especially alcanols having from 6 to 36 carbon atoms; alcenols having from 10 to 30 carbon atoms; glycols and triols such as di- and tri-pentaerythritol, trimethylolethane, anhydroenneahepitol, butanetriol, hexanetriol, erythritols, threitols, ribitol, arabinitols, xylitol, allitol, dulcitol, glucitol, sorbitol, mannitol, altritol, iditol, maltitol, lactitol, ethyleneglycol, diethyleneglycol, triethyleneglycol, trimethyleneglycol, tetramethyleneglycol, pentamethyleneglycol, hexamethyleneglycol, propyleneglycol, butyleneglycol, glycerol, diglycerol, 2,3-butanediol, 1,3-butanediol, sorbitol; mono-, di-, tri-, tetra-, and poly-amines, such as diethylenetriamine and ethanolamines; amides, e.g., acetamide and formamide, dimethylformamide, hexamethyl phosphotriamide; sulfoxides, e.g., dimethylsulfoxide, piperazines.

As already these lists of possible compounds are sometimes overlapping due to the fact that some compounds may have more than one agricultural effect. Activators or compatibility agents may also be used and may also be synergists or penetrating agents or stickers or spreaders or antidotes. Chelating agents may also be included in one or the other kind of hereabove mentionned adjuvants.

According to another feature, the ratio of volume between the outer bag and the inner bag is more than 1.5:1, preferably more than 2:1.

According to another feature, the ratio of weight of agrochemicals contained respectively in the outer bag and in the inner bag(s) is approximately equal to the ratio of the use rates of (or recommended for) the active ingredients contained respectively in the outer bag and the inner bag(s). Approximately equal means equal to the said ratio of the use rates or to a value which is in the range of plus or minus 10% of the said ratio of the use rates.

According to another feature of the invention the inner bag(s) and the outer bag contain respectively incompatible hazardous products, especially incompatible agrochemicals.

According to another feature of the invention both outer and inner bags can float or sink when put into water, such as the tank of water that a farmer uses for mixing and spraying.

According to still another feature of the invention which is particularly appropriate for incompatible or very incompatible agrochemicals, one of the bags (either an inner bag or the outer bag) floats and the other (or its content; preferably the outer bag) sinks when put into water. These specific bags are particularly suitable for very incompatible agrochemicals, whereby these incompatible agrochemicals, due to the fact that one bag floats and the other sinks, are separately diluted and mixed with water before being intermixed with each other.

When it is said that the inner bag floats and the outer bag sinks when put into water, that means that, when put into water, the inner bag(s) filled with its content, or its content alone (when the said inner bag has dissolved), float(s) when the outer bag is open (that is to say when the enveloping film of the outer bag has dissolved enough to let its content move) and when, at the same time, this partially opened outer bag (before it has completely dissolved) and its content (before or after this outer bag has completely dissolved) sink.

When it is said that the outer bag floats and the inner bag(s) sinks when put into water, that means that, when put into water, the inner bag(s) filled with its content, or its content alone (when the said inner bag has dissolved), sink(s) when the outer bag is open (that is to say when the enveloping film of the outer bag has dissolved enough to let its content move) and when, at the same time, this partially opened outer bag (before it has completely dissolved) and its content (before or after this inner bag has completely dissolved) float.

According to a particular feature of the invention, wherein one bag is floating and the other is sinking, the floating bag contains a wettable powder or water dispersible granules.

According to a particular feature of the invention which is of particular interest, the bags of the invention are made in such a way that the outer bag, either with its full content or with only the agrochemical composition which is outside the inner bag, may have a specific gravity greater than 1 and the inner bag, with its content, may have a specific gravity less than 1.

According to a particular feature of the invention which is of particular interest, the bags of the invention are made in such a way that the outer bag, either with its full content or with only the agrochemical composition which is outside the inner bag, may have a specific gravity less than 1 and the inner bag, with its content, may have a specific gravity greater than 1.

According to another feature, the bags of the invention, especially the outer bag, are filled to at least 60% of capacity with the agrochemical composition, more preferably to at least 70% of capacity, still more preferably 80 to 99% of capacity and most preferably 85 to 95% of capacity. The outer bag is preferably not filled to complete capacity because the unused capacity gives the shock resistance, i.e., resistance to breakage when dropped, transported or stored. This unused capacity may or may not contain air or inert gas. An absence of air or inert gas in the unused capacity further improves shock resistance. However in deciding how much unused capacity, or absence of air or inert gas, to provide, the advantages of shock resistance must be balanced against the need, if any, for shock resistance and the cost of providing shock resistance. For example, if the outer bag is stored and/or transported in a shock absorbing container, then it may not be as helpful to provide this unused capacity.

Also, the capacity to which the outer bag is filled, and whether the unused capacity does or does not contain air is affected by whether it is desired to have the bag sink or float.

Whether the bag sinks or floats will depend not only on the unused capacity, but also the specific gravity of the bag contents.

The percentage of capacity to which the inner bag is filled is more dictated, than is the capacity of the outer bag, by whether it is desired that the inner bag would sink or float. For example, compatibility of the bag contents and dispersibility of the bag contents in water affects whether it is desired to have the inner bag and the outer bag both float, or both sink, or have one bag sink and the other bag float. For example, if the active ingredients, or their formulations, contained by the inner or outer bags are compatible and dispersible even if both bags break open in the same part of the mixing bath, then it may be desirable to have both bags float or both bags sink.

When the bag is filled with solids, the capacity is relative to bulk volume of the solids, not the actual particle volume of the solids.

According to another feature of the invention, the inner bag may contain a marker, e.g. a dye. This marker is released to show if the inner bag has failed for any reason so that the package should not be used.

In practice the agrochemical compositions used in the instant invention generally comprises the active ingredient(s) in association with other ingredients, for example surfactants, dispersants, thickeners, antifoaming, antifreezing, gelled agents or gelling agents, plasticizers of the polymeric material constituting the enveloping film of the bags.

According to another feature the bags used in the invention are preferably made of a polymeric water soluble film. The thickness of this film is generally between 10 and 500 microns, preferably between 20 and 100 microns.

The polymeric material constituting the wall of the bags may be the same or may be different for the two bags. Eventhough these two bags may be differents, they are preferably cold water soluble. Cold water soluble means completely soluble in water at temperature lower than 35° C., for example comprised between 5° C. and 35° C. Both inner and outer bags may dissolve in water in similar conditions, that is to say in the same range of temperature as hereinbefore defined.

The chemical nature of the enveloping film constituting the bags can vary quite widely. Suitable materials are water soluble (or possibly water dispersible) materials which are insoluble in the organic solvents used to dissolve or disperse the agrochemical active ingredient.

Specific suitable materials include polyethylene oxide, such as polyethylene glycol; starch and modified starch; alkyl and hydroxyalkylcellulose, such as hydroxymethylcellulose, hydroxyethylcellulose, hydroxypropyl cellulose; carboxymethylcellulose; polyvinylethers such as poly methyl vinylether or poly(2-methoxyethoxyethylene); poly(2,4-dimethyl-6-triazinylethylene; poly(3-morpholinyl ethylene); poly(N-1,2,4-triazolylethylene); poly(vinylsulfonic acid); polyanhydrides; low molecular weight melamine-formaldehyde resins; low molecular weight ureaformaldehyde resins; poly(2-hydroxyethyl methacrylate); polyacrylic acid and its homologs. Preferably the enveloping film comprises or is made from polyvinylalcohol (PVA). PVA is generally partially or fully alcoholysed or hydrolysed e.g. 40-100%, preferably 80-99% alcoholysed or hydrolysed, polyvinyl acetate (or other ester) film; copolymers or other derivatives of such polymers can also be used.

Preferred materials for constituting the bags in the invention are polyethylene oxide or methylcellulose, or polyvinylalcohol. When polyvinylalcohol is used, it is advantageously a 40-100% alcoholysed or hydrolysed, preferably 80-99% alcoholysed or hydrolysed, polyvinyl acetate film.

The poly-bag system of the instant invention may be used by the farmer by simply putting the system into a tank of water and mixing or recirculating to get the ingredients homogeneously dispersed.

Accordingly, by another feature of the present invention, the poly-bag system is put into a tank of water. Then the farmer waits until the inner bag disassociates from the outer bag and its contents start to leak out. Then the mixing or recirculating starts only after that time. As already said, the bags may float or sink.

An advantage of the instant invention is that it prevents users from opening one package and to try and use only a part of one or the other package. Thus the invention provides a far safer system to apply two compounds to crops. It is safer both for the user and for the crop or plant.

The preparation or manufacturing of the containerization system of the invention can be done according the known process of preparation or manufacturing of water soluble bags. As a practical manner, the first bag (that is to say the inner bag, or inner bags if more than one) is prepared from a water soluble film, optionally by partial heat sealing. Then it is filled with an agrochemical composition and the bag(s) is finally closed. Then the second bag (that is to say the outer bag) is prepared in the same way. However, it is filled not only by an agrochemical composition, but also with the first bag(s) previously prepared. This later outer bag is also closed, preferably by heat sealing.

An advantage of the present invention is to have an easy way to obtain a two-components active unit. Its manufacturing is rather easy and does not need a real mixing system.

A particular embodiment of the invention is a containerization system which comprises at least one inner cold water soluble bag containing an agrochemical selected in the group comprising plant protection agents, pesticides, insecticides, herbicides, fungicides, nematocides, acaricides, plant nutrients, plant growth regulators, the containerization system further comprising an outer cold water soluble bag containing another hazardous compound different from the first and selected in the group comprising activity promoters, penetrating agents, synergists, antidotes, sticking agents, spreaders, activators, compatibility agents, adjuvants for the cold water soluble bags, plasticizers, the outer bag also containing the inner bag with its content.

Another particular embodiment of the invention is a containerization system which comprises at least one inner cold water soluble bag containing an agrochemical selected in the group comprising plant protection agents, pesticides, insecticides, herbicides, fungicides, nematocides, acaricides, plant nutrients, plant growth regulators, the containerization system further comprising an outer cold water soluble bag containing another hazardous compound different from the first and selected in the group comprising activity promoters, penetrating agents, synergists, antidotes, sticking agents, spreaders, activators, compatibility agents, adjuvants for the cold water soluble bags, plasticizers, the outer bag also containing the inner bag with its content, wherein the agrochemicals and the wall of the bags they contact are chosen so that the agrochemicals do not substantially dissolve the wall of the bag they contact and do not substantially permeate through it.

Another particular embodiment of the invention is a containerization system which comprises at least one inner cold water soluble bag containing an agrochemical selected in the group comprising plant protection agents, pesticides, insecticides, herbicides, fungicides, nematocides, acaricides, plant nutrients, plant growth regulators, the containerization system further comprising an outer cold water soluble bag containing another hazardous compound different from the first and incompatible with it and selected in the group comprising activity promoters, penetrating agents, synergists, antidotes, sticking agents, spreaders, activators, compatibility agents, adjuvants for the cold water soluble bags, plasticizers, the outer bag also containing the inner bag with its content.

Another particular embodiment of the invention is a containerization system which comprises at least one inner cold water soluble bag containing an agrochemical selected in the group comprising plant protection agents, pesticides, insecticides, herbicides, fungicides, nematocides, acaricides, plant nutrients, plant growth regulators, the containerization system further comprising an outer cold water soluble bag containing another hazardous compound different from the first and incompatible with it and selected in the group comprising activity promoters, penetrating agents, synergists, antidotes, sticking agents, spreaders, activators, compatibility agents, adjuvants for the cold water soluble bags, plasticizers, the outer bag also containing the inner bag with its content, wherein the agrochemicals and the wall of the bags they contact are chosen so that the agrochemicals do not substantially dissolve the wall of the bag they contact and do not substantially permeate through it.

Another particular embodiment of the invention is a containerization system which comprises at least one inner cold water soluble bag containing an agrochemical selected in the group comprising plant protection agents, pesticides, insecticides, herbicides, fungicides, nematocides, acaricides, plant nutrients, plant growth regulators, the containerization system further comprising an outer cold water soluble bag containing another hazardous compound different from the first and selected in the group comprising activity promoters, penetrating agents, synergists, antidotes, sticking agents, spreaders, activators, compatibility agents, adjuvants for the cold water soluble bags, plasticizers, the outer bag also containing the inner bag with its content, and wherein one of the bags, either an inner bag or the outer bag, float(s) when put into water and the other, or its content, sinks when put into water.

Another particular embodiment of the invention is a containerization system which comprises at least one inner cold water soluble bag containing an agrochemical selected in the group comprising plant protection agents, pesticides, insecticides, herbicides, fungicides, nematocides, acaricides, plant nutrients, plant growth regulators, the containerization system further comprising an outer cold water soluble bag containing another hazardous compound different from the first and selected in the group comprising activity promoters, penetrating agents, synergists, antidotes, sticking agents, spreaders, activators, compatibility agents, adjuvants for the cold water soluble bags, plasticizers, the outer bag also containing the inner bag with its content, wherein the agrochemicals and the wall of the bags they contact are chosen so that the agrochemicals do not substantially dissolve the wall of the bag they contact and do not substantially permeate through it, and wherein one of the bags, either an inner bag or the outer bag, float(s) when put into water and the other, or its content, sinks when put into water.

Another particular embodiment of the invention is a containerization system which comprises at least one inner cold water soluble bag containing an agrochemical selected in the group comprising plant protection agents, pesticides, insecticides, herbicides, fungicides, nematocides, acaricides, plant nutrients, plant growth regulators, the containerization system further comprising an outer cold water soluble bag containing another hazardous compound different from the first and incompatible with it and selected in the group comprising activity promoters, penetrating agents, synergists, antidotes, sticking agents, spreaders, activators, compatibility agents, adjuvants for the cold water soluble bags, plasticizers, the outer bag also containing the inner bag with its content, and wherein one of the bags, either an inner bag or the outer bag, float(s) when put into water and the other, or its content, sinks when put into water.

Another particular embodiment of the invention is a containerization system which comprises at least one inner cold water soluble bag containing an agrochemical selected in the group comprising plant protection agents, pesticides, insecticides, herbicides, fungicides, nematocides, acaricides, plant nutrients, plant growth regulators, the containerization system further comprising an outer cold water soluble bag containing another hazardous compound different from the first and incompatible with it and selected in the group comprising activity promoters, penetrating agents, synergists, antidotes, sticking agents, spreaders, activators, compatibility agents, adjuvants for the cold water soluble bags, plasticizers, the outer bag also containing the inner bag with its content, wherein the agrochemicals and the wall of the bags they contact are chosen so that the agrochemicals do not substantially dissolve the wall of the bag they contact and do not substantially permeate through it, and wherein one of the bags, either an inner bag or the outer bag, float(s) when put into water and the other, or its content, sinks when put into water.

Another particular embodiment of the invention is a containerization system according to any previous particular embodiment which comprises a further water insoluble external container.

Another particular embodiment of the invention is a containerization system according to any previous particular embodiment wherein the agrochemicals in the bags are in solid and/or liquid and/or gel form.

Another particular embodiment of the invention is a containerization system according to any previous particular embodiment wherein the inner bag(s) float(s)

when put into water and the outer bag sinks when put into water.

Another particular embodiment of the invention is a containerization system according to any previous particular embodiment wherein the inner bag(s) sink(s) when put into water and the outer bag floats when put into water.

Another particular embodiment of the invention is a containerization system according to any previous particular embodiment wherein the outer bag, either with its full content or with only the agrochemical composition which is outside the inner bag, has a specific gravity greater than 1 and the inner bag, with its content, has a specific gravity less than 1.

Another particular embodiment of the invention is a containerization system according to any previous particular embodiment wherein the outer bag, either with its full content or with only the agrochemical composition which is outside the inner bag, has a specific gravity less than 1 and the inner bag, with its content, has a specific gravity greater than 1.

Another particular embodiment of the invention is a containerization system according to any previous particular embodiment wherein the agrochemicals are in a concentrated form.

Another particular embodiment of the invention is a containerization system according to any previous particular embodiment wherein the concentrations of active ingredients in the agrochemicals in the bags are in the range from 0.5 to 80% (w/w) of active ingredient.

Another particular embodiment of the invention is a containerization system according to any previous particular embodiment wherein at least one bag contains an agrochemical composition in the form of water wettable powder or water dispersible granule.

Another particular embodiment of the invention is a containerization system according to any previous particular embodiment wherein one bag floats and contains wettable powder or water dispersible granules.

Another particular embodiment of the invention is a containerization system according to any previous particular embodiment wherein one bag contains a non-aqueous liquid in the form of a solution or a dispersion or an emulsion.

Another particular embodiment of the invention is a containerization system according to any previous particular embodiment wherein the ratio of weight of the hazardous compounds or agrochemicals contained respectively in the outer bag and in the inner bag is equal to a value which is in the range of plus or minus 10% of the ratio of the use rates of the active ingredients contained respectively in the outer bag and the inner bag.

Another particular embodiment of the invention is a containerization system according to any previous particular embodiment wherein the ratio of volume between the outer bag and the inner bag is more than 1.5:1.

Another particular embodiment of the invention is a containerization system according to any previous particular embodiment wherein the ratio of volume between the outer bag and the inner bag is more than 2:1.

Another particular embodiment of the invention is a containerization system according to any previous particular embodiment wherein at least one bag contains an agrochemical composition in the form of a non-aqueous liquid or in the form of an organic gel.

Another particular embodiment of the invention is a containerization system according to any previous particular embodiment wherein at least one bag contains an agrochemical composition in the form of an organic gel, and the organic gel has a viscosity of 600 to 30,000 centipoise.

Another particular embodiment of the invention is a containerization system according to any previous particular embodiment wherein at least one bag contains an agrochemical composition in the form of an organic gel, and the organic gel has a viscosity of 1,000 to 12,000 centipoise.

Another particular embodiment of the invention is a containerization system according to any previous particular embodiment wherein at least one of the agrochemical compositions is an organic gel, and the organic gel has a phase difference phi between the controlled shear stress and the resulting shear strain such that tg(phi) is less than or equal to 1.5.

Another particular embodiment of the invention is a containerization system according to any previous particular embodiment wherein at least one of the agrochemical compositions is an organic gel, and the organic gel has a phase difference phi between the controlled shear stress and the resulting shear strain such that tg(phi) is less than or equal to 1.2.

Another particular embodiment of the invention is a containerization system according to any previous particular embodiment wherein the inner bag contains a marker.

Another particular embodiment of the invention is a containerization system according to any previous particular embodiment wherein the outer bag is filled with said second agrochemical and said inner bag to at least 60% of capacity.

Another particular embodiment of the invention is a containerization system according to any previous particular embodiment wherein at least one of the agrochemical compositions is a liquid which has a Brookfield viscosity between 100 and 30,000 centipoise.

Another particular embodiment of the invention is a containerization system according to any previous particular embodiment wherein at least one of the agrochemical compositions is a liquid which has a Brookfield viscosity between 1000 and 30,000 centipoise.

Further information may be found in the following copending applications, the disclosures of which are incorporated herein by reference: U.S. Ser. No. 07/713,681, application of David B. Edwards, William J. Mc Carthy, Leonard E. Hodakowski, Chi-Yu R. Chen, Samuel T. Gouge and Paul J. Weber for "Laminated Bags for containerization of Toxic or Hazardous Materials" filed Jun. 11, 1991; U.S. Ser. No. 07/713,682, application of Samuel T. Gouge, Leonard E. Hodakowski, Paul J. Weber and Chi-Yu R. Chen for "Gel Formulations for Hazardous Products" filed Jun. 11, 1991; U.S. Ser. No. 07/713,701, application of Leonard E. Hodakowski, Chi-Yu R. Chen, Samuel T. Gouge and Paul J. Weber for "Water Dispersible Gel Formulations" filed Jun. 11, 1991; U.S. Ser. No. 07/713,685, application of Leonard E. Hodakowski, Ricky W. Couch, Samuel T. Gouge and Robert C. Ligon for "Gel Formulations" filed Jun. 11, 1991; and U.S. Ser. No. 07/713,683, application of Leonard E. Hodakowski, Chi-Yu R. Chen, Samuel T. Gouge and Paul J. Weber for "Gel Formulations for Use in Toxic or Hazardous Product Containerization Systems" filed Jun. 11, 1991.

The following examples are given for illustrative purposes and should not be understood as restricting the invention.

In these examples, the Brookfield viscosity was measured, as previously indicated, with a Brookfield viscosimeter which had a flat plate rotating at 20 revolutions per minute at 20° C.

In all the following examples, the prepared gels had a tg(phi) of between 0.1 and 1.5.

EXAMPLE 1

A package was made by placing a water soluble bag filled with a solid (wettable powder) insecticide into a larger water soluble bag filled with a liquid sticker-spreader.

The film used in this experiment was a laminated film of polyvinyl alcohol with a total thickness of 75 microns (half for each layer).

25 g of a cypermethrin (in wettable powder form) was poured into a small water soluble bag made of polyvinyl alcohol. This wettable powder contained surfactants in a sufficient amount so as to promote dispersion/wetting of the active ingredient into water.

450 g of the spreading/sticking agent Nu-Film 17 (di-1-p-menthene) was poured into a large water soluble polyvinyl alcohol bag. The smaller bag filled with the cypermethrin was also added to this large bag filled with the sticker-spreader. The large bag was then sealed by heat sealing.

This large bag with its content was dropped into a tank filled to 68 gallons of water with 342 ppm hardness. This large bag floated on the water surface. This bag began to dissolve and after approximately 1 minute 70 seconds, small amounts of the spreader-sticker began to leak from the dissolving bag and slowly emulsify into the water. After another 22 seconds the small bag (filled with pyrethroid) also separated from the larger bag. After an additional 55 seconds the small bag began to dissolve and release the cypermethrin wettable powder into the water. This wettable powder and the spreader sticker quickly mixed with the water as soon as the recirculation pump was turned on. After 1 additional minute both pyrethroid and sticker/spreader were completely mixed into the water. The mixture was pumped out of the tank. There were no problems observed by nozzle pluggage or by screen blockage or by sediment left on the tank bottom.

In this example, the wettable powder, as well as the liquid spray adjuvant (spreader/sticker) floated due to their density and air left in the bags.

EXAMPLE 2

A package was made by placing a water soluble bag filled with a solid water dispersible powder herbicide into a larger water soluble bag filled with a thickened liquid spreading and penetrating adjuvant.

The film used in this experiment was a laminated film of polyvinyl alcohol with a total thickness of 75 microns.

50 g of an 75% sulfonyl urea water dispersible powder was poured into a small water soluble bag made of polyvinyl alcohol. The granules contained surfactants in a sufficient amount so as to promote rapid dispersion.

1000 g of spray adjuvant (Bio 88-water free; mixture of alkylpolyethoxy ethanol+free fatty acids+isopropanol) was poured into a large water soluble polyvinyl alcohol bag. The smaller filled with sulfonyl urea herbicide WDG was also added to this large bag filled with Bio 88 adjuvant. This large bag was then sealed by heat sealing.

This large bag with its content was dropped into a tank filled to 18 gallons of water with 342 ppm hardness. This large bag floated on the water surface. This bag began to dissolve and after approximately 1.45 minutes, releasing the thickened liquid adjuvant into the water. After an additional 30 seconds, the small bag (filled with sulfonyl urea) was also released from the dissolving bag. This small bag dissolved allowing the powder to flow from it onto the water surface. This powder quickly mixed with the water as soon as the recirculation pump was turned on. After approximately 2 additional minutes of recirculation, the floating water dispersible powder dispersed completely into the water mix. There were no problems observed by nozzle pluggage or by screen blockage or by sediment left on the tank bottom.

In this example, the water dispersible powder, as well as the liquid adjuvant are floating because of their air content and low specific gravity.

EXAMPLE 3

A small package was made by placing a water soluble bag filled with a water-dispersible granule herbicide (atrazine) into a larger water soluble bag filled with a crop oil concentrate adjuvant.

The film used in this experiment was a laminated film of polyvinyl alcohol with a total thickness of 75 microns.

75 g of a sulfonylurea water dispersible granule herbicide was used to fill a small water soluble polyvinyl alcohol bag. The bag was then heat sealed.

950 ml of a crop oil concentrate was poured into a larger water soluble bag made of polyvinyl alcohol. The smaller bag filled with atrazine was also placed inside this larger bag filled with the crop oil concentrate. This large bag with its content was then heat sealed.

This large bag with its content was dropped into a tank of water (60 liters). This large floated on the water surface and began to dissolve. After approximately 1.7 minutes, it released a small pocket of air at the bottom side of the bag. Twelve seconds later, the small bag full of atrazine water dispersible granules began to spill out of the dissolving polyvinyl alcohol bag and disperse into water. After an additional 57 seconds, the water dispersible granules had wetted in water and dispersed into water. The pump recirculation system was started. This immediately mixed the gel into the tank of water with the atrazine. The mixture was sprayed through the nozzles and final examination showed no sedimentation or pluggage in the nozzles, filters or on the tank bottom.

EXAMPLE 4

A package was made by placing a water soluble bag filled with a liquid leaf penetrant into a larger water soluble bag filled with a solid wettable powder insecticide.

The film used in this experiment was laminated film of polyvinyl alcohol with a total thickness of 75 microns.

100 g of a Penetrator (spray adjuvant which is a mixture of paraffin petroleum base+polyol fatty acid esters+polyethoxylated polyol fatty acid esters) was poured into a small water soluble bag made of polyvinyl alcohol.

1200 g of carbaryl wettable powder (80% of carbaryl in the powder) was poured into a large water soluble polyvinyl alcohol bag. The smaller bag filled with the Penetrator was also added to this large bag filled with carbaryl water dispersible granule. This large bag was then sealed by heat sealing.

This large bag with its content was dropped into a tank filled to 60 l with water (hardness: 342 ppm). This large bag floated on the water surface. This bag began to dissolve and, after approximately 1 minute 20 seconds, released its contents including the small bag (filled with Penetrator adjuvant). This small bag began to dissolve into the cloudy water mixture. After 1 minute 10 seconds the liquide broke and diluted itself into the water. The pump recirculation was started and the materials readily mixed inside the tank.

The contents was sprayed through the nozzles and final examination showed no sedimentation or pluggage or residue in the nozzles, filters or on the tank bottom.

What is claimed is:

1. A containerization system which comprises at least one inner cold water soluble bag containing an agrochemical selected in the group comprising plant protection agents, pesticides, insecticides, herbicides, fungicides, nematocides, acaricides, plant nutrients, plant growth regulators, the containerization system further comprising an outer cold water soluble bag containing another hazardous compound different from the first and selected in the group comprising activity promoters, penetrating agents, synergists, antidotes, sticking agents, spreaders, activators, compatibility agents, adjuvants for the cold water soluble bags, plasticizers, the outer bag also containing the inner bag with its content wherein the inner bag sinks and the outer bag floats when put into water.

2. A containerization system which comprises at least one inner cold water soluble bag containing an agrochemical selected in the group comprising plant protection agents, pesticides, insecticides, herbicides, fungicides, nematocides, acaricides, plant nutrients, plant growth regulators, the containerization system further comprising an outer cold water soluble bag containing another hazardous compound different from the first and selected in the group comprising activity promoters, penetrating agents, synergists, antidotes, sticking agents, spreaders, activators, compatibility agents, adjuvants for the cold water soluble bags, plasticizers, the outer bag also containing the inner bag with its contents, wherein the agrochemicals and the wall of the bags they contact are chosen so that the agrochemicals do not substantially dissolve the wall of the bag they contact and do not substantially permeate through it wherein the inner bag sinks and the outer bag floats when put into water.

3. A containerization system which comprises at least one inner cold water soluble bag containing an agrochemical selected in the group comprising plant protection agents, pesticides, insecticides, herbicides, fungicides, nematocides, acaricides, plant nutrients, plant growth regulators, the containerization system further comprising an outer cold water soluble bag containing another hazardous compound different from the first and incompatible with it and selected in the group comprising activity promoters, penetrating agents, synergists, antidotes, sticking agents, spreaders, activators, compatibility agents, adjuvants for the cold water soluble bags, plasticizers, the outer bag also containing the inner bag with its content wherein the inner bag sinks and the outer bag floats when put into water.

4. A containerization system which comprises at least one inner cold water soluble bag containing an agrochemical selected in the group comprising plant protection agents, pesticides, insecticides, herbicides, fungicides, nematocides, acaricides, plant growth regulators, the containerization system further comprising an outer cold water soluble bag containing another hazardous compound different from the first and incompatible with it and selected in the group comprising activity promoters, penetrating agents, synergists, antidotes, sticking agents, spreaders, activators, compatibility agents, adjuvants for the cold water soluble bags, plasticizers, the outer bag also containing the inner bag with its content, wherein the agrochemicals and the wall of the bags they contact are chosen so that the agrochemicals do not substantially dissolve the wall of the bag they contact and do not substantially permeate through it wherein the inner bag sinks and the outer bag floats when put into water.

* * * * *